US012277626B2

(12) United States Patent
Takahashi

(10) Patent No.: US 12,277,626 B2
(45) Date of Patent: Apr. 15, 2025

(54) INFORMATION PROCESSING APPARATUS, INFORMATION PROCESSING SYSTEM, INFORMATION PROCESSING METHOD, AND INFORMATION PROCESSING PROGRAM

(71) Applicant: FUJIFILM Corporation, Tokyo (JP)

(72) Inventor: Azuma Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 253 days.

(21) Appl. No.: 17/715,931

(22) Filed: Apr. 7, 2022

(65) Prior Publication Data

US 2022/0230367 A1    Jul. 21, 2022

Related U.S. Application Data

(63) Continuation of application No. PCT/JP2020/039419, filed on Oct. 20, 2020.

(30) Foreign Application Priority Data

Dec. 10, 2019 (JP) ................................ 2019-223151

(51) Int. Cl.
  *G06T 11/00*  (2006.01)
(52) U.S. Cl.
  CPC .......... *G06T 11/006* (2013.01); *G06T 11/003* (2013.01); *G06T 2207/10132* (2013.01); *G06T 2211/441* (2023.08)
(58) Field of Classification Search
  CPC .................................................. G06T 11/003
  See application file for complete search history.

(56) References Cited

U.S. PATENT DOCUMENTS 10,548,572 B2 * 2/2020 Susumu .............. G01S 7/52095
2004/0236220 A1 * 11/2004 Willis .................. A61B 8/0833
                                                            600/443

(Continued)

FOREIGN PATENT DOCUMENTS

JP    2005058378      3/2005
JP    2006280963     10/2006

(Continued)

OTHER PUBLICATIONS

"International Search Report (Form PCT/ISA/210) of PCT/JP2020/039419," mailed on Dec. 22, 2020, with English translation thereof, pp. 1-5.

(Continued)

*Primary Examiner* — Oneal R Mistry
*Assistant Examiner* — Duy Tran
(74) *Attorney, Agent, or Firm* — JCIPRNET

(57) ABSTRACT

The CPU 20 obtains a three-dimensional image 50 that is a captured image of an organ of a subject and obtains a plurality of ultrasound tomographic images 56 that are images of the organ successively captured at different positions. The CPU 20 identifies, for each ultrasound tomographic image 56 among the plurality of ultrasound tomographic images 56, a CT tomographic image 49 corresponding to a cross section the same as a cross section to which the ultrasound tomographic image 56 corresponds, among a plurality of CT tomographic images 49 that constitute the three-dimensional image 50, and associates position information indicating a position corresponding to the identified CT tomographic image 49 with the ultrasound tomographic image 56 among the plurality of ultrasound tomographic images 56. The CPU 20 generates a three-dimensional ultrasound image 58 from the plurality of (Continued)

ultrasound tomographic images 56 on the basis of the position information.

10 Claims, 5 Drawing Sheets

(56) References Cited

U.S. PATENT DOCUMENTS

| | | | | |
|---|---|---|---|---|
| 2008/0306379 | A1* | 12/2008 | Ikuma | G16H 50/50 600/424 |
| 2013/0057547 | A1* | 3/2013 | Hwang | G06T 19/00 345/420 |
| 2014/0171800 | A1* | 6/2014 | Kondou | A61B 5/066 600/440 |
| 2015/0087981 | A1* | 3/2015 | Ishii | G01S 7/52065 600/443 |
| 2017/0150942 | A1 | 6/2017 | Fujita et al. | |
| 2019/0355174 | A1* | 11/2019 | Endo | A61B 8/5246 |
| 2020/0051257 | A1* | 2/2020 | Sauer | G06T 7/344 |
| 2020/0129147 | A1* | 4/2020 | Nair | A61B 8/469 |
| 2021/0015452 | A1* | 1/2021 | Shimizu | A61B 5/0073 |
| 2021/0113191 | A1* | 4/2021 | Zou | A61B 8/483 |
| 2022/0395333 | A1* | 12/2022 | Merritt | A61B 6/5241 |

FOREIGN PATENT DOCUMENTS

| | | |
|---|---|---|
| JP | 2013223792 | 10/2013 |
| JP | 2017099603 | 6/2017 |

OTHER PUBLICATIONS

"Written Opinion of the International Searching Authority (Form PCT/ISA/237)" of PCT/JP2020/039419, mailed on Dec. 22, 2020, with English translation thereof, pp. 1-7.

* cited by examiner

INFORMATION PROCESSING APPARATUS, INFORMATION PROCESSING SYSTEM, INFORMATION PROCESSING METHOD, AND INFORMATION PROCESSING PROGRAM

This application is a Continuation of PCT International Application No. PCT/JP2020/039419 filed on Oct. 20, 2020, which claims priority under 35 U.S.C § 119(a) to Japanese Patent Application No. 2019-223151 filed on Dec. 10, 2019. Each of the above application(s) is hereby expressly incorporated by reference, in its entirety, into the present application.

BACKGROUND OF THE INVENTION

1. Field of the Invention

The present disclosure relates to an information processing apparatus, an information processing system, an information processing method, and a non-transitory computer recording medium storing an information processing program.

2. Description of the Related Art

Techniques for generating a three-dimensional ultrasound image from ultrasound images captured by an ultrasound imaging apparatus are currently known. For example, JP2005-58378A discloses a technique in which the insertion and placement position of an ultrasound probe inserted into a surgical site is calculated and a three-dimensional ultrasound image is generated on the basis of the calculated insertion position.

SUMMARY OF THE INVENTION

With techniques of the related art, in a case where ultrasound images for obtaining a three-dimensional ultrasound image are captured, hardware for measuring the position of, for example, an ultrasound probe is necessary in order to obtain position information of the imaging position. Therefore, the size of the entire ultrasound imaging apparatus may increase or the size of the ultrasound probe may increase.

With the technique disclosed in JP2005-58378A described above, a navigation apparatus including a zoom encoder that detects the zoom magnification of an observation optical system displaying an enlarged observation optical image of a surgical site, a focus encoder that detects the focal length of the observation optical system, and a digitizer is used to calculate the insertion and placement position of the ultrasound probe. Therefore, with the technique disclosed in JP2005-58378A, hardware including the digitizer is necessary, and the size of the entire ultrasound imaging apparatus increases accordingly.

The present disclosure has been made in view of the above-described circumstances and provides an information processing apparatus, an information processing system, an information processing method, and a non-transitory computer recording medium storing an information processing program that can generate a three-dimensional ultrasound image from ultrasound images captured without using hardware for measuring the imaging position.

To achieve the object described above, an information processing apparatus according to a first aspect of the present disclosure includes: at least one processor; and a memory configured to store an instruction executable by the processor, the processor being configured to obtain a three-dimensional image that is a captured image of an organ of a subject, obtain a plurality of ultrasound tomographic images that are images of the organ successively captured at different positions, identify, for each ultrasound tomographic image among the plurality of ultrasound tomographic images, a tomographic image corresponding to a cross section the same as a cross section to which the ultrasound tomographic image corresponds, among a plurality of tomographic images that constitute the three-dimensional image, and associate position information indicating a position of the cross section corresponding to the identified tomographic image with the ultrasound tomographic image among the plurality of ultrasound tomographic images, and generate a three-dimensional ultrasound image from the plurality of ultrasound tomographic images on the basis of the position information.

An information processing apparatus according to a second aspect of the present disclosure is the information processing apparatus according to the first aspect, in which the processor is configured to identify the tomographic image corresponding to the cross section the same as the cross section to which the ultrasound tomographic image corresponds by carrying out an image analysis for each of the plurality of ultrasound tomographic images and for each of the plurality of tomographic images.

An information processing apparatus according to a third aspect of the present disclosure is the information processing apparatus according to the first or second aspect, in which the processor is configured to perform control to display the three-dimensional ultrasound image.

An information processing apparatus according to a fourth aspect of the present disclosure is the information processing apparatus according to the first or second aspect, in which the processor is configured to perform control to display the three-dimensional image such that the cross section corresponding to each of the obtained ultrasound tomographic images is recognizable.

An information processing apparatus according to a fifth aspect of the present disclosure is the information processing apparatus according to any one of the first to fourth aspects, in which the processor is configured to perform control to display each of the obtained ultrasound tomographic images.

An information processing apparatus according to a sixth aspect of the present disclosure is the information processing apparatus according to any one of the first to fifth aspects, in which the processor is configured to obtain the plurality of ultrasound tomographic images from an ultrasound imaging apparatus that captures ultrasound tomographic images of the organ of the subject with an ultrasonic endoscope inserted into a body cavity of the subject.

To achieve the object described above, an information processing system according to a seventh aspect of the present disclosure includes: a three-dimensional imaging apparatus that captures a three-dimensional image of an organ of a subject; an ultrasound imaging apparatus that successively captures ultrasound tomographic images of the organ at different positions; and the information processing apparatus according to any one of claims 1 to 6 that obtains the three-dimensional image from the three-dimensional imaging apparatus and that obtains the plurality of ultrasound tomographic images from the ultrasound imaging apparatus.

To achieve the object described above, an information processing method according to an eighth aspect of the present disclosure is an information processing method in which a computer performs a process including: obtaining a three-dimensional image that is a captured image of an organ of a subject; obtaining a plurality of ultrasound tomographic images that are images of the organ successively captured at different positions; identifying, for each ultrasound tomographic image among the plurality of ultrasound tomographic images, a tomographic image corresponding to a cross section the same as a cross section to which the ultrasound tomographic image corresponds, among a plurality of tomographic images that constitute the three-dimensional image, and associating position information indicating a position of the cross section corresponding to the identified tomographic image with the ultrasound tomographic image among the plurality of ultrasound tomographic images; and generating a three-dimensional ultrasound image from the plurality of ultrasound tomographic images on the basis of the position information.

To achieve the object described above, a non-transitory computer recording medium storing an information processing program according to a ninth aspect of the present disclosure is a non-transitory computer recording medium storing an information processing program for causing a computer to perform a process including: obtaining a three-dimensional image that is a captured image of an organ of a subject; obtaining a plurality of ultrasound tomographic images that are images of the organ successively captured at different positions; identifying, for each ultrasound tomographic image among the plurality of ultrasound tomographic images, a tomographic image corresponding to a cross section the same as a cross section to which the ultrasound tomographic image corresponds, among a plurality of tomographic images that constitute the three-dimensional image, and associating position information indicating a position of the cross section corresponding to the identified tomographic image with the ultrasound tomographic image among the plurality of ultrasound tomographic images; and generating a three-dimensional ultrasound image from the plurality of ultrasound tomographic images on the basis of the position information.

According to the present disclosure, it is possible to generate a three-dimensional ultrasound image from ultrasound images captured without using hardware for measuring the imaging position.

DESCRIPTION OF THE PREFERRED EMBODIMENTS

Hereinafter, an example embodiment of the technique of the present disclosure will be described in detail below with reference to the attached drawings. In the present embodiment, a description will be given of a form in which an organ of a subject that is an imaging target is the large intestine, and more specifically, the inside of the large intestine.

Figure 1:
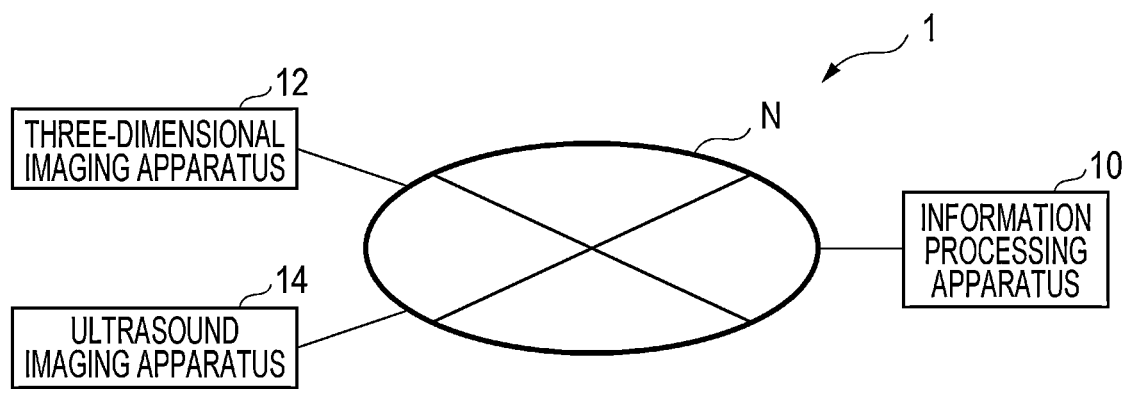
FIG. 1 is a block diagram illustrating an example configuration of an information processing system.

First, an information processing system 1 of the present embodiment will be described with reference to FIG. 1. FIG. 1 is a block diagram illustrating an example configuration of the information processing system 1 of the present embodiment. As illustrated in FIG. 1, the information processing system 1 of the present embodiment includes an information processing apparatus 10, a three-dimensional imaging apparatus 12, and an ultrasound imaging apparatus 14. The information processing apparatus 10 and the three-dimensional imaging apparatus 12 are connected to a network N so as to be able to communicate with each other over the network N. The information processing apparatus 10 and the ultrasound imaging apparatus 14 are connected to the network N so as to be able to communicate with each other over the network N.

The information processing apparatus 10 is, for example, a personal computer that is installed in a hospital where examinations of subjects are conducted. Note that the information processing apparatus 10 may be, for example, a tablet computer or a smartphone or may be a cloud server configured in a cloud. The information processing apparatus 10 may be constituted by a plurality of apparatuses, such as a combination of a cloud server and a tablet computer.

The three-dimensional imaging apparatus 12 is an imaging apparatus that captures a three-dimensional image of an organ of a subject. Examples of the three-dimensional imaging apparatus 12 include imaging apparatuses capable of capturing three-dimensional CT images by using, for example, MDCT (Multi Detector row Computed Tomography) or helical CT and imaging apparatuses capable of capturing three-dimensional MRI images by using MRI (Magnetic Resonance Imaging). In the present embodiment, for example, the three-dimensional imaging apparatus 12 is an imaging apparatus that generates a three-dimensional image of the inside of the large intestine of a subject from a plurality of CT images captured by using CT in a 3D (three-dimensional) examination of the large intestine of the subject. The three-dimensional imaging apparatus 12 is an apparatus that generates virtual endoscopic images of the inside of the large intestine of the subject from the CT images. The three-dimensional imaging apparatus 12 outputs the three-dimensional image and the virtual endoscopic images of the inside of the large intestine of the subject.

The ultrasound imaging apparatus 14 is an imaging apparatus that captures an ultrasound image of an organ of a subject. In the present embodiment, for example, the ultrasound imaging apparatus 14 is an imaging apparatus that captures an ultrasound tomographic image of an organ of a subject with an ultrasonic endoscope that has an ultrasound probe provided with an ultrasound transducer at the distal end of an endoscope to be inserted into the body cavity of the subject. More specifically, in the present embodiment, the ultrasound imaging apparatus 14 is an imaging apparatus that generates an ultrasound tomographic image of the large intestine from each of the plurality of ultrasound images successively captured in time series with the ultrasonic endoscope inserted into the large intestine of the subject. In the present embodiment, images are successively captured while the ultrasonic endoscope of the ultrasound imaging apparatus 14 is moved, and therefore, the ultrasound imaging apparatus 14 outputs a plurality of ultrasound tomographic images successively captured at different positions. The ultrasound imaging apparatus 14 of the present embodiment includes the ultrasonic endoscope as described above. Therefore, the ultrasound imaging apparatus 14 also captures endoscopic images that are optical images with the endoscope of the ultrasonic endoscope. The ultrasound imaging apparatus 14 outputs the ultrasound tomographic images each corresponding to a corresponding one of the plurality of cross sections of the large intestine of the subject and the endoscopic images each corresponding to a corresponding one of the plurality of cross sections of the large intestine of the subject.

Figure 2:
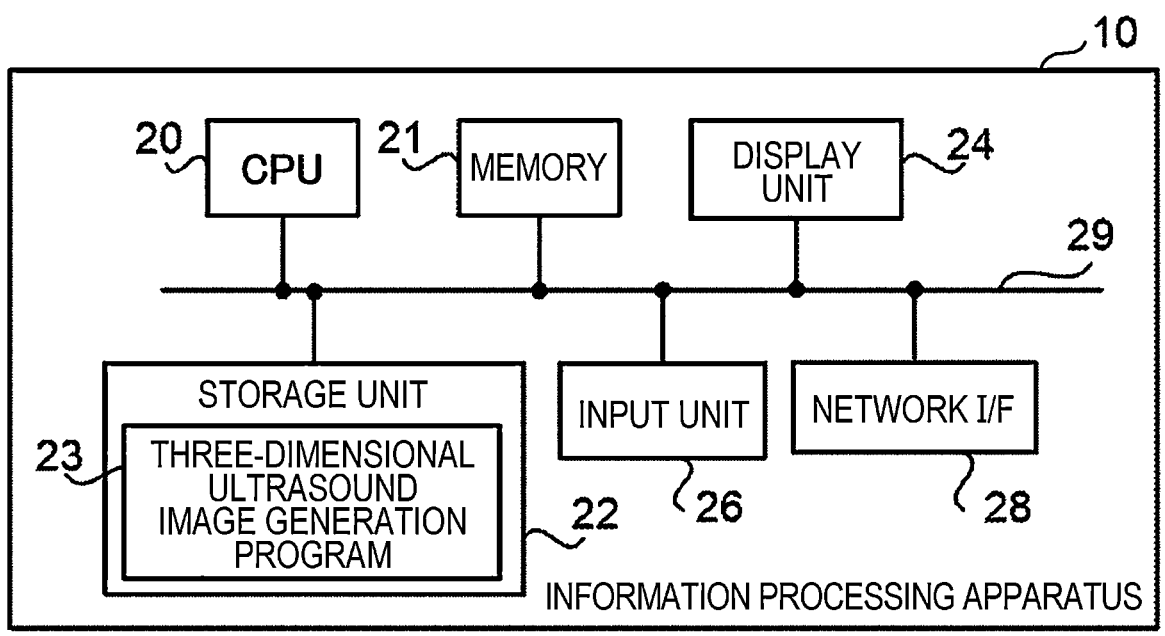
FIG. 2 is a block diagram illustrating an example hardware configuration of an information processing apparatus.

Next, an example hardware configuration of the information processing apparatus 10 of the present embodiment will be described with reference to FIG. 2. As illustrated in FIG. 2, the information processing apparatus 10 includes a CPU (central processing unit) 20, a memory 21, which is a temporary memory area, and a storage unit 22, which is a nonvolatile memory. The CPU 20 of the present embodiment is an example of a processor in the present disclosure, and the storage unit 22 is an example of a memory in the present disclosure.

The information processing apparatus 10 includes a display unit 24, which is, for example, a liquid crystal display, an input unit 26, which is, for example, a keyboard or a mouse, and a network I/F (interface) 28, which is connected to the network N. Note that the display unit 24 and the input unit 26 may be integrated into a touch panel display. The CPU 20, the memory 21, the storage unit 22, the display unit 24, the input unit 26, and the network I/F 28 are connected to a bus 29 so as to be able to communicate with each other.

The storage unit 22 is implemented as, for example, an HDD (hard disk drive), an SSD (solid state drive), or a flash memory. In the storage unit 22 that is a storage medium, a three-dimensional ultrasound image generation program 23 is stored. The CPU 20 reads from the storage unit 22 and loads to the memory 21 the three-dimensional ultrasound image generation program 23 and executes the loaded three-dimensional ultrasound image generation program 23. The three-dimensional ultrasound image generation program 23 of the present embodiment is an example of the information processing program in the present disclosure.

Figure 3:
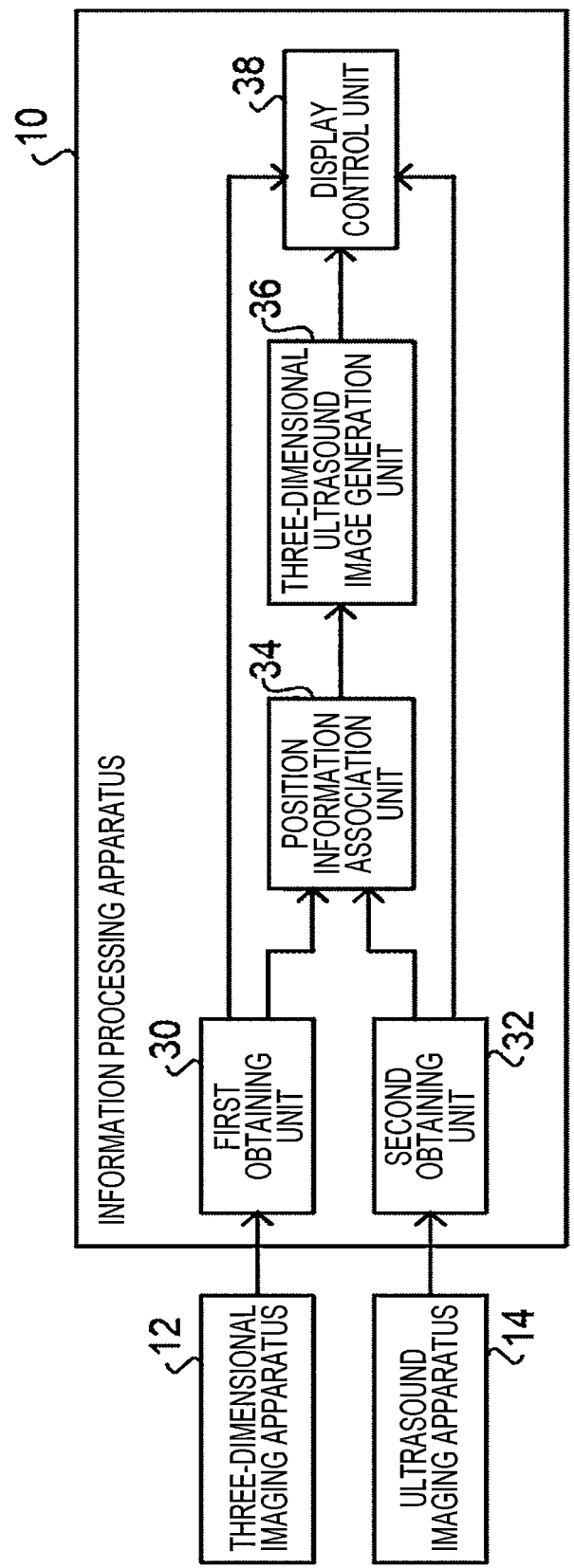
FIG. 3 is a block diagram illustrating an example functional configuration of the information processing apparatus.

Next, a functional configuration of the information processing apparatus 10 of the present embodiment will be described with reference to FIG. 3. As illustrated in FIG. 3, the information processing apparatus 10 includes a first obtaining unit 30, a second obtaining unit 32, a position information association unit 34, a three-dimensional ultrasound image generation unit 36, and a display control unit 38. The CPU 20 executes the three-dimensional ultrasound image generation program 23 to thereby function as the first obtaining unit 30, the second obtaining unit 32, the position information association unit 34, the three-dimensional ultrasound image generation unit 36, and the display control unit 38.

The first obtaining unit 30 obtains a three-dimensional image of an organ of a subject from the three-dimensional imaging apparatus 12. For example, the first obtaining unit 30 of the present embodiment obtains a three-dimensional image and virtual endoscopic images of the inside of the large intestine of a subject output from the three-dimensional imaging apparatus 12 as described above. For example, voxel data created on the basis of imaging data obtained by the three-dimensional imaging apparatus 12 such as CT is used to extract the large intestine region and create a three-dimensional image of the inside of the large intestine. Accordingly, virtual endoscopic images can be created on the basis of any viewpoint positions and directions in the inside of the large intestine, and cross-section images at any positions in the large intestine can be created. The first obtaining unit 30 outputs the obtained three-dimensional image to the position information association unit 34. The first obtaining unit 30 outputs the obtained three-dimensional image and virtual endoscopic images to the display control unit 38.

The second obtaining unit 32 obtains from the ultrasound imaging apparatus 14 a plurality of ultrasound images and a plurality of endoscopic images obtained by successive time-series imaging of an organ of a subject. For example, the second obtaining unit 32 of the present embodiment obtains ultrasound tomographic images each corresponding to a corresponding one of the plurality of cross sections of the large intestine of the subject and endoscopic images each corresponding to a corresponding one of the plurality of cross sections of the large intestine of the subject output from the ultrasound imaging apparatus 14 as described above. The second obtaining unit 32 outputs the obtained ultrasound images (ultrasound tomographic images) to the position information association unit 34. The second obtaining unit 32 outputs the obtained ultrasound images (ultrasound tomographic images) and endoscopic images to the display control unit 38.

Figure 4:
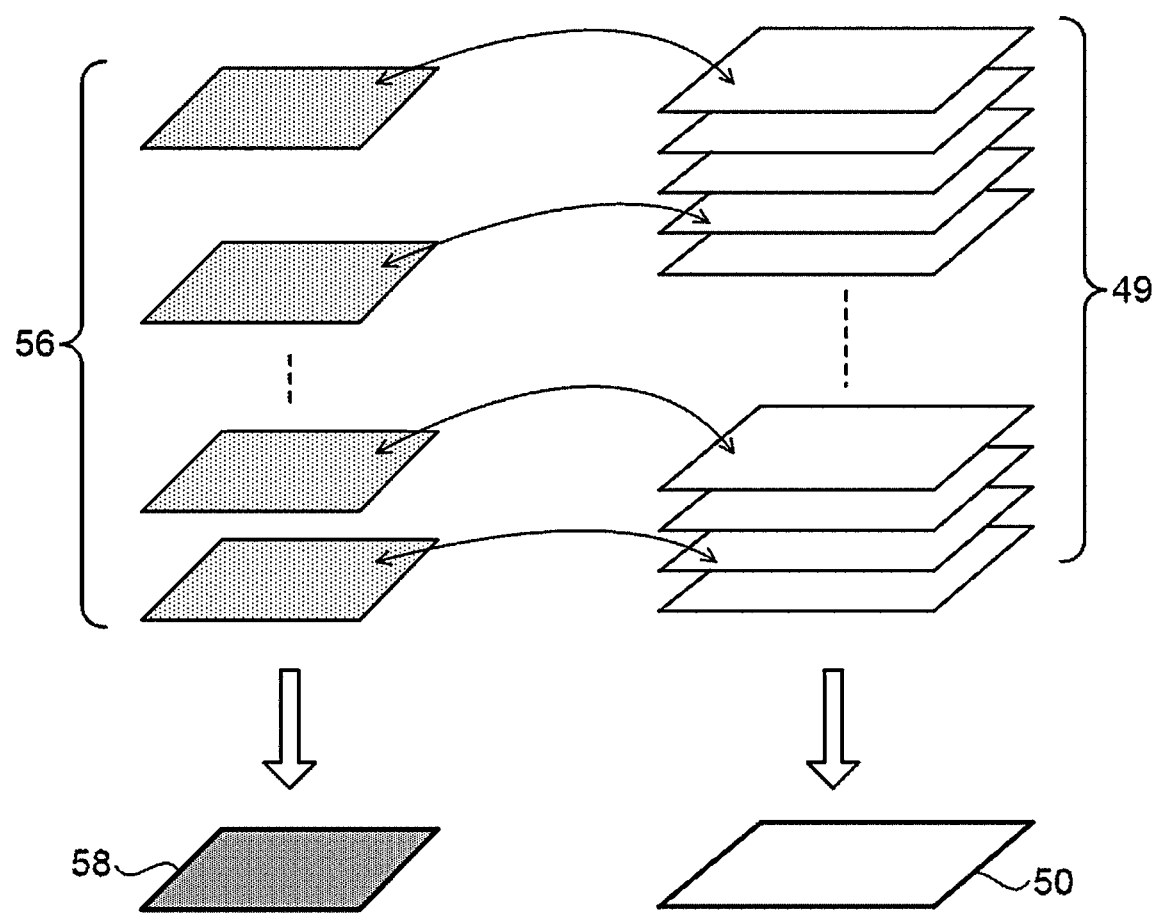
FIG. 4 is a diagram for explaining generation of a three-dimensional ultrasound image by the information processing apparatus.

As illustrated in FIG. 4, for each ultrasound tomographic image 56 among a plurality of ultrasound tomographic images 56 obtained by the second obtaining unit 32, the position information association unit 34 identifies a CT tomographic image corresponding to a cross section the same as a cross section to which the ultrasound tomographic image 56 corresponds, among a plurality of tomographic images 49 that constitute a three-dimensional image 50 obtained by the first obtaining unit 30. In order to distinguish the plurality of tomographic images 49 that constitute the three-dimensional image 50 from the ultrasound tomographic images 56, the tomographic images 49 are hereinafter referred to as CT tomographic images 49. Note that the CT tomographic images 49 are preferably tomographic images corresponding to cross sections in any directions based on the voxel data.

In the present embodiment, as illustrated in FIG. 4, the position information association unit 34 identifies, for each ultrasound tomographic image 56 among the plurality of ultrasound tomographic images 56, the CT tomographic image 49 corresponding to a cross section the same as a cross section to which the ultrasound tomographic image 56 corresponds, among the plurality of CT tomographic images 49 that constitute the three-dimensional image of the inside of the large intestine. Although there is no limitation on the method for identifying the CT tomographic image 49 corresponding to a cross section the same as a cross section to which the ultrasound tomographic image 56 corresponds, it is preferable that an image analysis be carried out for each of the ultrasound tomographic images 56 and each of the CT tomographic images 49 to extract feature values, and the CT tomographic image 49 be identified on the basis of the extracted feature values. Examples of the technique for the image analysis include techniques, such as contrast conversion, noise removal, histogram conversion, pattern matching, and edge detection, and statistical image processing techniques including robust image processing.

For example, a form may be employed in which the CT tomographic image 49 is identified by using artificial intelligence (AI). Examples of using AI include a method in which AI that uses a trained model generated by learning a combination of an ultrasound tomographic image and a CT tomographic image of the same cross section as learning data (also called teacher data) is used. The trained model in this case is generated so as to, on the basis of input of the plurality of CT tomographic images 49 that constitute the three-dimensional image and the plurality of ultrasound tomographic images 56, output position information (for example, three-degree-of-freedom position or three-degree-of-freedom rotation) of the CT tomographic image 49 corresponding to a cross section the same as a cross section to which the ultrasound tomographic image 56 corresponds. Another specific example of the trained model is a trained model generated so as to, on the basis of the CT tomographic images, output pseudo (or virtual) ultrasound tomographic images. In a case of this trained model, the position information association unit 34 selects a pseudo ultrasound tomographic image that is most analogous to the ultrasound tomographic image 56 and identifies the CT tomographic image 49 that corresponds to the selected pseudo ultrasound tomographic image as the CT tomographic image 49 corresponding to a cross section the same as a cross section to which the ultrasound tomographic image 56 corresponds. As the learning algorithms of these trained models, for example, the backpropagation algorithm can be used.

For example, a form may be employed in which virtual endoscopic images corresponding to the CT tomographic images 49 are used to identify the CT tomographic image 49 corresponding to a cross section the same as a cross section to which the ultrasound tomographic image 56 corresponds. The CT tomographic images 49 correspond to virtual endoscopic images, and therefore, combinations of the virtual endoscopic images and the ultrasound tomographic image 56 are learned in advance, and position information to which an unknown virtual endoscopic image and the ultrasound tomographic image 56 correspond is identified (output). The virtual endoscopic images can be easily associated with the ultrasound tomographic images 56, and therefore, the virtual endoscopic images can be used to facilitate identification of the CT tomographic image 49.

Unlike in a case where the inside of the large intestine is imaged as in the present embodiment, in a case where an image of a relatively hard organ, such as a bone, or an image of a characteristic organ for which the position and the shape can be identified is included in the ultrasound tomographic images 56 and in the CT tomographic images 49, a form may be employed in which segmentation is performed for the image of the organ in each tomographic image, and the CT tomographic image 49 corresponding to a cross section the same as a cross section to which the ultrasound tomographic image 56 corresponds is identified on the basis of the result of segmentation. A trained model that learns a combination of an ultrasound tomographic image and a CT tomographic image of the same cross section as learning data and also learns the results of segmentation performed for the ultrasound tomographic image and the CT tomographic image is used. When the results of segmentation of the ultrasound tomographic image and the CT tomographic image (for example, the shape and position information of, for example, the organ) are also learned as ground truth data, improvement in the accuracy of identification of a position to which an unknown virtual endoscopic image and the ultrasound tomographic image 56 correspond can be expected.

Each CT tomographic image 49 of the present embodiment is associated with position information for identifying the position of a cross section that correspond to the CT tomographic image 49. For example, the position information is information indicating the position and rotation of any cross section that corresponds to the CT tomographic image 49 in the voxel data. For each ultrasound tomographic image 56 among the plurality of ultrasound tomographic images 56, the position information association unit 34 assumes the position of a cross section indicated by position information associated with the identified CT tomographic image 49 to be the position of a cross section corresponding to the ultrasound tomographic image 56. That is, the position information association unit 34 associates position information indicating a position corresponding to the identified CT tomographic image 49 with the ultrasound tomographic image 56 as position information of the ultrasound tomographic image 56.

The three-dimensional ultrasound image generation unit 36 generates a three-dimensional ultrasound image 58 from the plurality of ultrasound tomographic images 56 on the basis of pieces of position information associated with the ultrasound tomographic images 56 by the position information association unit 34, as illustrated in FIG. 4. From the pieces of position information associated with the ultrasound tomographic images, the position and interval of each ultrasound tomographic image 56 are derived. The three-dimensional ultrasound image generation unit 36 layers the plurality of ultrasound tomographic images 56 on the basis of the derived positions and intervals to thereby generate the three-dimensional ultrasound image 58.

The display control unit 38 performs control to display the ultrasound tomographic image 56, the three-dimensional ultrasound image 58, an endoscopic image, and a virtual endoscopic image corresponding to the same cross section on the display unit 24. The display control unit 38 performs control to display the three-dimensional image 50 obtained from the three-dimensional imaging apparatus 12 such that the position of the cross section can be recognized.

Figure 5:
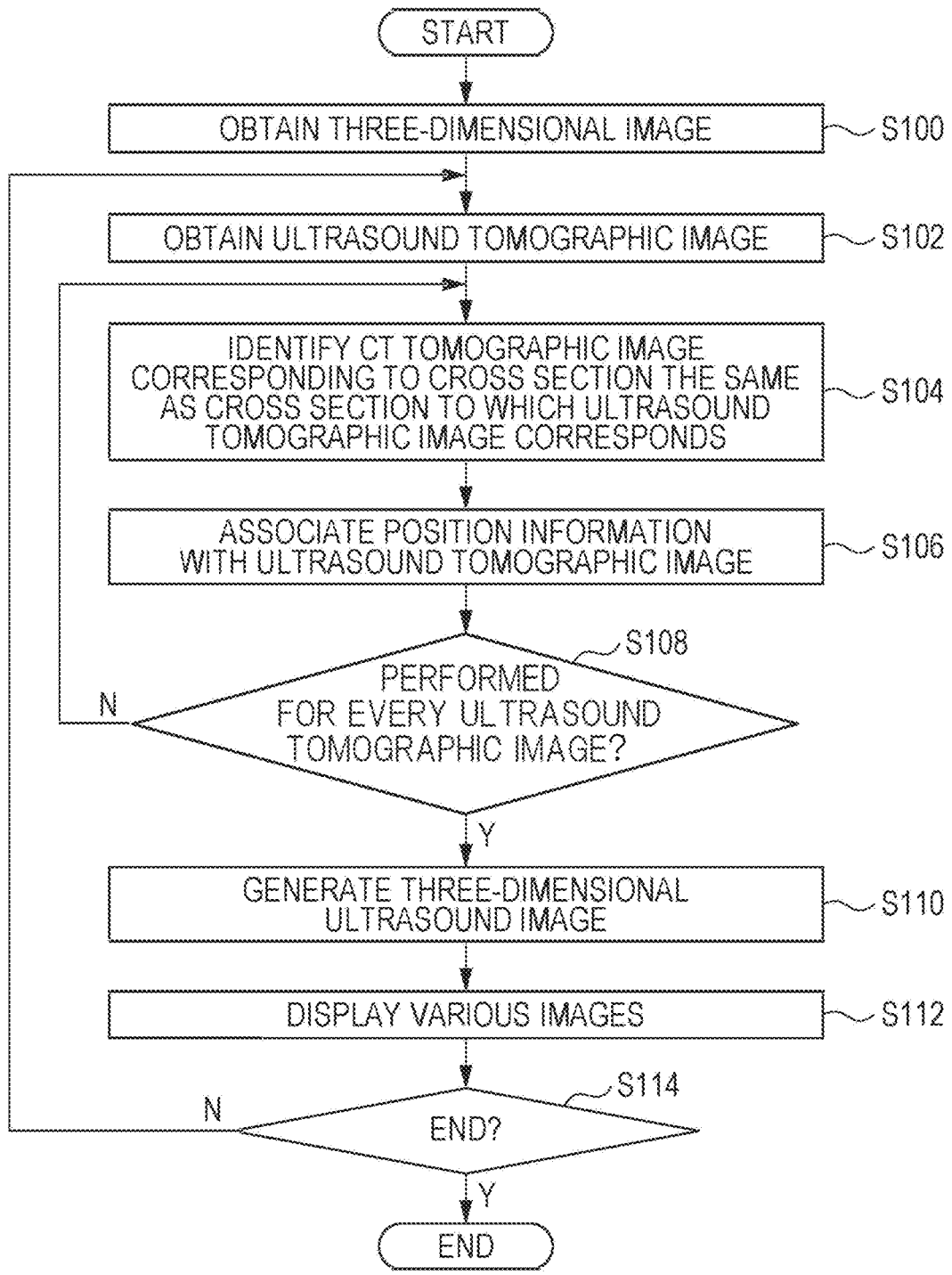
FIG. 5 is a flowchart illustrating an example of a three-dimensional ultrasound image generation process that is performed by the information processing apparatus.

Next, operations of the information processing apparatus 10 of the present embodiment will be described with reference to FIG. 5. A three-dimensional ultrasound image generation process illustrated in FIG. 5 is performed by the CPU 20 executing the three-dimensional ultrasound image generation program 23. The three-dimensional ultrasound image generation process illustrated in FIG. 5 is performed in response to, for example, an instruction for generating a three-dimensional ultrasound image input by a user operating the input unit 26. The timing when the three-dimensional ultrasound image generation process of the present embodiment is performed needs to be a timing after a three-dimensional image is captured in advance by the three-dimensional imaging apparatus 12, and image capturing by the ultrasound imaging apparatus 14 can be performed simultaneously with image capturing by the three-dimensional imaging apparatus 12. For example, the three-dimensional ultrasound image generation process of the present embodiment can be performed in real time during an ultrasound endoscope examination.

In step S100 in FIG. 5, the first obtaining unit 30 obtains the three-dimensional image 50 from the three-dimensional imaging apparatus 12 as described above. The first obtaining unit 30 further obtains virtual endoscopic images from the three-dimensional imaging apparatus 12 as described above.

Next, in step S102, the second obtaining unit 32 obtains the ultrasound tomographic image 56 from the ultrasound imaging apparatus 14 as described above. The second obtaining unit 32 further obtains an endoscopic image from the ultrasound imaging apparatus 14 as described above.

Next, in step S104, the position information association unit 34 identifies the CT tomographic image 49 corresponding to a cross section the same as a cross section to which the ultrasound tomographic image 56 corresponds as described above. For example, when the plurality of ultrasound tomographic images 56 are obtained in step S102, the position information association unit 34 selects one of the obtained ultrasound tomographic images 56 and identifies the CT tomographic image 49 corresponding to a cross section the same as cross section to which the selected ultrasound tomographic image 56 corresponds.

Next, in step S106, the position information association unit 34 associates position information indicating the position of the corresponding cross section with the ultrasound tomographic image 56. Specifically, the position information association unit 34 assumes the position of a cross section indicated by position information associated with the CT tomographic image 49 identified in step S104 described above to be the position of the cross section corresponding to the selected ultrasound tomographic image 56. The position information association unit 34 associates the position information indicating the position of the cross section with the selected ultrasound tomographic image 56.

Next, in step S108, the position information association unit 34 determines whether position information indicating the position of a corresponding cross section is associated with every ultrasound tomographic image 56 obtained in step S102 described above, that is, whether the process in steps S104 and S106 described above has been performed for every ultrasound tomographic image 56. If there is the ultrasound tomographic image 56 for which the process in steps S104 and S106 described above is not yet performed, determination in step S108 results in negative determination, and the flow returns to step S104. The position information association unit 34 selects the ultrasound tomographic image 56 subsequent to the previously selected ultrasound tomographic image 56 in the time series order as the ultrasound tomographic image 56 different from any ultrasound tomographic image 56 selected previously and repeats the process in step S104 and step S106.

On the other hand, if the process in steps S104 and S106 described above has been performed for every ultrasound tomographic image 56 obtained in step S102 described above, determination in step S108 results in positive determination, and the flow proceeds to step S110.

In step S110, the three-dimensional ultrasound image generation unit 36 generates the three-dimensional ultrasound image 58 from the plurality of ultrasound tomographic images 56 as described above. Specifically, the three-dimensional ultrasound image generation unit 36 layers the plurality of ultrasound tomographic images 56 to generate the three-dimensional ultrasound image 58 on the basis of the position and interval of each of the plurality of ultrasound tomographic images 56 derived from the position information associated with each ultrasound tomographic image 56 in step S106 described above.

Figure 6:
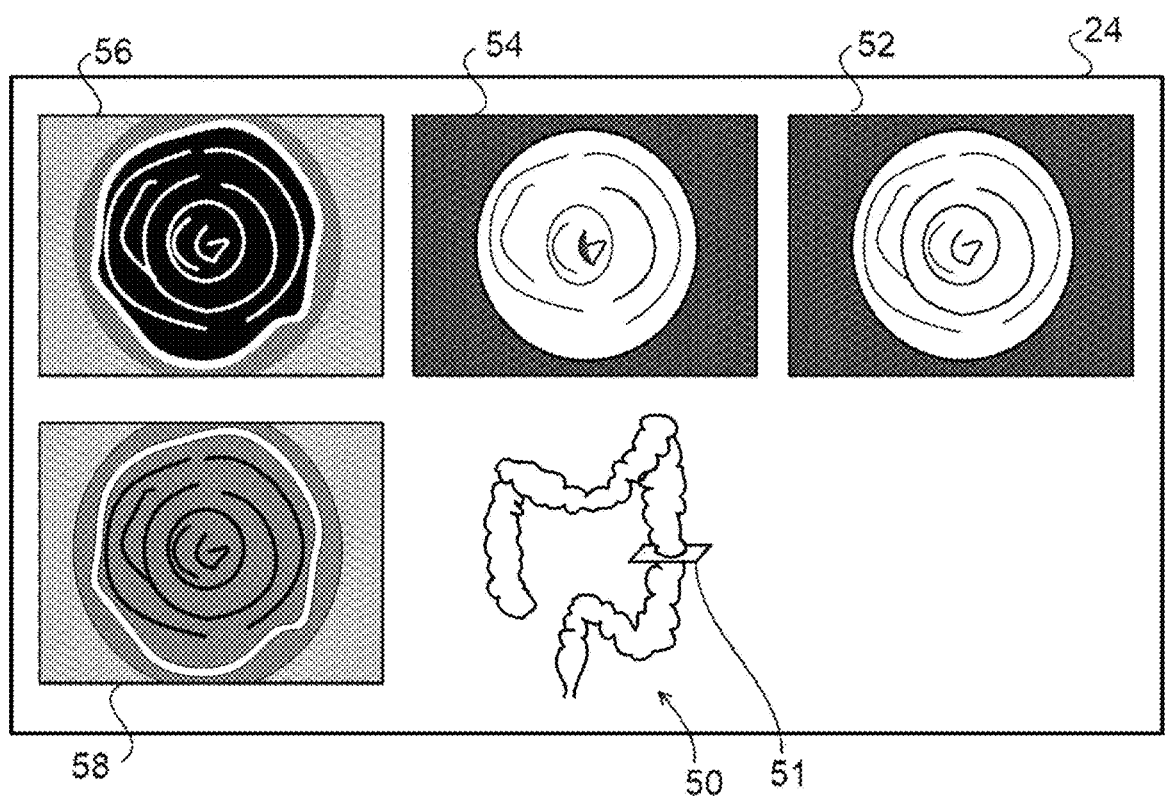
FIG. 6 is a diagram illustrating examples of a three-dimensional image, a virtual endoscopic image, an endoscopic image, an ultrasound tomographic image, and a three-dimensional ultrasound image displayed on a display unit of the information processing apparatus.

Next, in step S112, the display control unit 38 performs control to display the three-dimensional image 50, a virtual endoscopic image, an endoscopic image, the ultrasound tomographic image 56, and the three-dimensional ultrasound image 58 on the display unit 24. FIG. 6 illustrates examples of the three-dimensional image 50, a virtual endoscopic image 52, an endoscopic image 54, the ultrasound tomographic image 56, and the three-dimensional ultrasound image 58 displayed on the display unit 24. FIG. 6 illustrates an example where the virtual endoscopic image 52, the endoscopic image 54, and the ultrasound tomographic image 56 corresponding to the same cross section are displayed on the display unit 24 in accordance with the time series order of the ultrasound tomographic images 56. In the example illustrated in FIG. 6, the three-dimensional ultrasound image 58 based on the ultrasound tomographic image 56 captured by the ultrasound imaging apparatus 14 at the position of a cross section 51 is displayed on the display unit 24.

Further, in the example illustrated in FIG. 6, the three-dimensional image 50 is displayed on the display unit 24 such that the cross section 51 corresponding to the virtual endoscopic image 52, the endoscopic image 54, and the ultrasound tomographic image 56 can be recognized. As described above, the display unit 24 displays the ultrasound tomographic image 56 and so on in accordance with the time series order, and therefore, the position of the cross section 51 in the three-dimensional image 50 is a position corresponding to the displayed ultrasound tomographic image 56 and so on.

Note that unlike in the present embodiment, a form may be employed in which the display control unit 38 performs control to display the three-dimensional image 50, the virtual endoscopic image 52, the endoscopic image 54, the ultrasound tomographic image 56, and the three-dimensional ultrasound image 58 corresponding to a cross section that corresponds to a position specified by a user using, for example, the input unit 26.

For example, the display form and display method of each of the three-dimensional image 50, the virtual endoscopic image 52, the endoscopic image 54, the ultrasound tomographic image 56, and the three-dimensional ultrasound image 58 are not limited to the form illustrated in FIG. 6. For example, in a case where an image of a plurality of organs is included in the ultrasound tomographic images 56 and in the CT tomographic images 49, a form may be employed in which segmentation is performed for the image of the organs included in the CT tomographic images 49, and the ultrasound tomographic image 56 labeled with the names of the organs on the basis of the result of segmentation is displayed.

Next, in step S114, the display control unit 38 determines whether the three-dimensional ultrasound image generation process is to end. For example, in a case where the three-dimensional ultrasound image 58 and so on are displayed in real time as illustrated in the example in FIG. 6 by using the ultrasound tomographic images 56 and the endoscopic images 54 successively output from the ultrasound imaging apparatus 14 during an ultrasound endoscope examination, determination in step S114 results in negative determination. If determination in step S114 results in negative determination, the flow returns to step S102, and the process in steps S102 to S112 is repeated. On the other hand, for example, in a case where the three-dimensional ultrasound image generation process is performed after the end of an ultrasound endoscope examination and a predetermined end condition that, for example, an instruction for ending display is given by a user, determination in step S114 results in positive determination, and the three-dimensional ultrasound image generation process ends.

As described above, the information processing apparatus 10 of the present embodiment includes the CPU 20 and the storage unit 22 that stores instructions executable by the CPU 20. The CPU 20 obtains the three-dimensional image 50 that is a captured image of an organ of a subject and obtains the plurality of ultrasound tomographic images 56 that are images of the organ successively captured at different positions. The CPU 20 identifies, for each ultrasound tomographic image 56 among the plurality of ultrasound tomographic images 56, the CT tomographic image 49 corresponding to a cross section the same as a cross section to which the ultrasound tomographic image 56 corresponds, among the plurality of CT tomographic images 49 that constitute the three-dimensional image 50, and associates position information indicating a position corresponding to the identified CT tomographic image 49 with the ultrasound tomographic image 56 among the plurality of ultrasound tomographic images 56. The CPU 20 generates the three-dimensional ultrasound image 58 from the plurality of ultrasound tomographic images 56 on the basis of the position information.

Accordingly, the information processing apparatus 10 of the present embodiment associates position information indicating the position of each ultrasound tomographic image 56 among the plurality of ultrasound tomographic images 56 captured in time series with the ultrasound tomographic image 56 on the basis of the position of the CT tomographic image 49 corresponding to a cross section the same as a cross section to which the ultrasound tomographic image 56 corresponds. The positions of the CT tomographic images 49 that constitute the three-dimensional image 50 and that are captured in advance by the three-dimensional imaging apparatus 12 are known. Therefore, the information processing apparatus 10 of the present embodiment can generate a three-dimensional ultrasound image from ultrasound tomographic images captured without using hardware for measuring the imaging position of each ultrasound image captured by the ultrasound imaging apparatus 14, that is, specifically, the position of the ultrasound probe.

With the information processing apparatus 10 of the present embodiment, hardware for measuring the position of the ultrasound probe need not be used in capturing of ultrasound images, and therefore, an increase in the size of the entire ultrasound imaging apparatus or in the size of the ultrasound probe is suppressed.

Specifically, in imaging with an ultrasonic endoscope, an ultrasound probe is inserted into the body cavity of a subject, and therefore, as the size (the diameter) of the ultrasound probe increases, the stress of the subject increases. With the information processing apparatus 10 of the present embodiment, however, it is possible to suppress an increase in the size of (the diameter of) the ultrasound probe, and the stress of the subject can be reduced accordingly.

The information processing apparatus 10 of the present embodiment displays in real time the three-dimensional image 50 that includes the cross section 51 indicating the position of a cross section corresponding to the ultrasound tomographic image 56 captured by the ultrasound probe of the ultrasound imaging apparatus 14 during an ultrasound examination. The position of the cross section 51 in the three-dimensional image 50 corresponds to the position of the distal end of the ultrasound probe. Therefore, the information processing apparatus 10 of the present embodiment can show the position of the ultrasound probe with the cross section 51 in the three-dimensional image 50 during an ultrasound endoscope examination.

Although a form in which the ultrasound imaging apparatus 14 captures ultrasound tomographic images with the ultrasonic endoscope that is inserted into the body cavity of a subject has been described in the present embodiment, the ultrasound imaging apparatus 14 is not limited to this form. For example, a form may be employed in which the ultrasound imaging apparatus 14 captures ultrasound tomographic images by scanning the body surface of a subject with the ultrasound probe.

Although a case where the inside of the large intestine is an imaging target of ultrasound tomographic images in a 3D examination of the large intestine of a subject has been described in the present embodiment, the imaging target of ultrasound tomographic images is not limited to the inside of the large intestine. For example, other organs, such as the pancreas and the gallbladder, may be imaging targets of ultrasound tomographic images.

As the hardware configuration of processing units that perform various types of processing by, for example, the functional units of the information processing apparatus 10 according to the present embodiment, various processors described below can be used. The various processors include a CPU, which is a general-purpose processor executing software (program) as described above to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or two or more processors of the same type or different types (for example, a combination of a plurality of FPGAs or a combination of a CPU and an FPGA). Further, a plurality of processing units may be configured as one processor.

As the first example of configuring a plurality of processing units as one processor, a form is possible where one or more CPUs and software are combined to configure one processor, and the processor functions as the plurality of processing units, representative examples of which are computers, such as a client and a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, as the hardware configuration of the various processors, more specifically, an electric circuit (circuitry) in which circuit elements, such as semiconductor elements, are combined can be used.

Although a form in which the three-dimensional ultrasound image generation program 23 is stored (installed) in advance in the storage unit 22 has been described in the present embodiment, the three-dimensional ultrasound image generation program 23 is not limited to this. The three-dimensional ultrasound image generation program 23 may be recorded to a recording medium, such as a CD-ROM (compact disc read-only memory), a DVD-ROM (digital versatile disc read-only memory), or a USB (universal serial bus) memory, and provided. A form may be employed in which the three-dimensional ultrasound image generation program 23 is downloaded from an external apparatus over a network.

REFERENCE SIGNS LIST 1 information processing system
10 information processing apparatus
12 three-dimensional imaging apparatus
14 ultrasound imaging apparatus
20 CPU
21 memory
22 storage unit
23 three-dimensional ultrasound image generation program
24 display unit 26 input unit
28 network OF
29 bus
30 first obtaining unit
32 second obtaining unit
34 position information association unit
36 three-dimensional ultrasound image generation unit
38 display control unit
49 CT tomographic image
50 three-dimensional image
51 cross section
52 virtual endoscopic image
54 endoscopic image
56 ultrasound tomographic image
58 three-dimensional ultrasound image
N network

What is claimed is:

1. An information processing apparatus comprising:
at least one processor; and
a memory configured to store an instruction executable by the processor, wherein
the processor is configured to
   obtain a three-dimensional image that is a captured image of an organ of a subject, wherein the three-dimensional image is constituted by a plurality of tomographic images,
   obtain a plurality of ultrasound tomographic images that are images of the organ successively captured at different positions, wherein each of the plurality of ultrasound tomographic images corresponds to one of a plurality of cross sections of the organ,
   for each ultrasound tomographic image among the plurality of ultrasound tomographic images,
      identify a tomographic image, among the plurality of tomographic images, corresponding to the ultrasound tomographic image, wherein the ultrasound tomographic image and the identified tomographic image corresponds to a same cross section, and
      associate position information indicating a position of the cross section corresponding to the identified tomographic image with the ultrasound tomographic image, and
   generate a three-dimensional ultrasound image from the plurality of ultrasound tomographic images on the basis of the associated position information of each of the plurality of ultrasound tomographic images.

2. The information processing apparatus according to claim 1, wherein
the processor is configured to
identify the tomographic image corresponding to the cross section the same as the cross section to which the ultrasound tomographic image corresponds by carrying out an image analysis for each of the plurality of ultrasound tomographic images and for each of the plurality of tomographic images.

3. The information processing apparatus according to claim 1, wherein
the processor is configured to
perform control to display the three-dimensional ultrasound image.

4. The information processing apparatus according to claim 1, wherein
the processor is configured to
perform control to display the three-dimensional image such that the cross section corresponding to each of the obtained ultrasound tomographic images is recognizable.

5. The information processing apparatus according to claim 1, wherein
the processor is configured to
perform control to display each of the obtained ultrasound tomographic images.

6. The information processing apparatus according to claim 1, wherein
the processor is configured to
obtain the plurality of ultrasound tomographic images from an ultrasound imaging apparatus that captures ultrasound tomographic images of the organ of the subject with an ultrasonic endoscope inserted into a body cavity of the subject.

7. An information processing system comprising:
a three-dimensional imaging apparatus that captures a three-dimensional image of an organ of a subject;
an ultrasound imaging apparatus that successively captures ultrasound tomographic images of the organ at different positions; and
the information processing apparatus according to claim 1 that obtains the three-dimensional image from the three-dimensional imaging apparatus and that obtains the plurality of ultrasound tomographic images from the ultrasound imaging apparatus.

8. An information processing method in which a computer performs a process comprising:
obtaining a three-dimensional image that is a captured image of an organ of a subject, wherein the three-dimensional image is constituted by a plurality of tomographic images;
obtaining a plurality of ultrasound tomographic images that are images of the organ successively captured at different positions, wherein each of the plurality of ultrasound tomographic images corresponds to one of a plurality of cross sections of the organ;
for each ultrasound tomographic image among the plurality of ultrasound tomographic images,
   identifying a tomographic image, among the plurality of tomographic images, corresponding to the ultrasound tomographic image, wherein the ultrasound tomographic image and the identified tomographic image corresponds to a same cross section, and
   associating position information indicating a position of the cross section corresponding to the identified tomographic image with the ultrasound tomographic image; and
generating a three-dimensional ultrasound image from the plurality of ultrasound tomographic images on the basis of the associated position information of each of the plurality of ultrasound tomographic images.

9. A non-transitory computer recording medium storing an information processing program for causing a computer to perform a process comprising:
obtaining a three-dimensional image that is a captured image of an organ of a subject, wherein the three-dimensional image is constituted by a plurality of tomographic images;
obtaining a plurality of ultrasound tomographic images that are images of the organ successively captured at different positions, wherein each of the plurality of ultrasound tomographic images corresponds to one of a plurality of cross sections of the organ;

for each ultrasound tomographic image among the plurality of ultrasound tomographic images,
identifying a tomographic image, among the plurality of tomographic images, corresponding to the ultrasound tomographic image, wherein the ultrasound tomographic image and the identified tomographic image corresponds to a same cross section, and
associating position information indicating a position of the cross section corresponding to the identified tomographic image with the ultrasound tomographic image; and
generating a three-dimensional ultrasound image from the plurality of ultrasound tomographic images on the basis of the associated position information of each of the plurality of ultrasound tomographic images.

10. The information processing apparatus according to claim 1, wherein
the processor is configured to
set the position information indicating the position of the cross section corresponding to the identified tomographic image as the position information of the ultrasound tomographic image.

\* \* \* \* \*